US005928243A

United States Patent [19]
Guyer

[11] Patent Number: 5,928,243
[45] Date of Patent: Jul. 27, 1999

[54] PEDICLE PROBE AND DEPTH GAGE

[75] Inventor: Richard D. Guyer, Dallas, Tex.

[73] Assignee: Spinal Concepts, Inc., Austin, Tex.

[21] Appl. No.: 08/896,281

[22] Filed: Jul. 16, 1997

[51] Int. Cl.⁶ ................................................ A61B 17/56
[52] U.S. Cl. ............................................................ 606/102
[58] Field of Search ............................ 606/86, 102, 106; 433/72

[56] References Cited

U.S. PATENT DOCUMENTS

| | | |
|---|---|---|
| 4,401,112 | 8/1983 | Rezaian . |
| 4,433,677 | 2/1984 | Ulrich et al. . |
| 4,450,834 | 5/1984 | Fischer ...................................... 606/80 |
| 4,492,226 | 1/1985 | Belykh et al. . |
| 4,501,269 | 2/1985 | Bagby . |
| 4,503,848 | 3/1985 | Caspar et al. . |
| 4,570,618 | 2/1986 | Wu . |
| 4,604,995 | 8/1986 | Stephens et al. . |
| 4,641,636 | 2/1987 | Cotrel . |
| 4,643,178 | 2/1987 | Nastari et al. . |
| 4,743,256 | 5/1988 | Brantigan . |
| 4,763,644 | 8/1988 | Webb . |
| 4,805,602 | 2/1989 | Puno et al. . |
| 4,834,757 | 5/1989 | Brantigan . |
| 4,878,915 | 11/1989 | Brantigan . |
| 4,887,596 | 12/1989 | Sherman . |
| 4,946,458 | 8/1990 | Harmes et al. . |
| 4,950,269 | 8/1990 | Gaines, Jr. . |
| 4,961,740 | 10/1990 | Ray et al. . |
| 4,966,600 | 10/1990 | Songer et al. . |
| 4,987,892 | 1/1991 | Krag et al. . |
| 5,005,562 | 4/1991 | Cotrel . |
| 5,026,373 | 6/1991 | Ray et al. . |
| 5,047,029 | 9/1991 | Aebi et al. . |
| 5,055,104 | 10/1991 | Ray . |
| 5,074,864 | 12/1991 | Cozad et al. . |
| 5,102,412 | 4/1992 | Rogozinski . |
| 5,108,399 | 4/1992 | Eitenmuller et al. . |
| 5,108,446 | 4/1992 | Wagner et al. . |

(List continued on next page.)

OTHER PUBLICATIONS

Spinal Concepts, Inc., "The BacFix—Posterior Lower Back Fixation System Written Surgical Technique," Aug. 1997, pp. 1–11.

Danek Group, Inc. Medical Division Publication entitled, "TSRH Spinal System—Unmatched versatility," 1992, pp. 1–4.

Danek Surgical Technique Manual entitled, "TSRH Spinal Implant System," Date Unknown, pp. 1–16.

Danek Surgical Technique Manual entitled, "TSRH Crosslink," Date Unknown, pp. 1–8.

Dickman Curtis A., BNI Quarterly Publication entitled, "Techniques of Screw Fixation of the Cervical Spine," vol. 9. No. 4, Fall 1993, pp. 27–39.

Slone et al., RadioGraphics Publication entitled, "Spinal Fixation," vol. 13 No. 2, Mar. 1993, pp. 341–356.

Synthes Spine Publication entitled, "The Universal Spinal System—Internal Fixation for the Spine," 1994, pp. 1–15.

AcroMed Publication entitled, "The ISOLA Spinal System—Versatility, simplicity and minimal profile in the surgical treatment of the spine," 1994, pp. 1–15.

AcroMed Corporation Publication entitled, "ISOLA® Transverse Rod Connectors: Principles and Techniques," Date Unknown, pp. i. ii, 1–8.

(List continued on next page.)

*Primary Examiner*—Michael Buiz
*Assistant Examiner*—David O. Reip
*Attorney, Agent, or Firm*—Conley, Rose & Tayon, P.C.

[57] ABSTRACT

A bone probe and method for using the same. The bone probe preferably includes a body having an interior cavity for containing an arm and a shaft that are slideably mounted within the body. The shaft and the arm preferably extend from opposite sides of the body and are preferably removably connected to one another. The shaft is preferably substantially flexible and may include a probing end for contacting an interior surface of a bone opening to locate surface irregularities within the bone opening. The arm preferably includes a plurality of reference markings for measuring a depth of the bone opening.

22 Claims, 1 Drawing Sheet

U.S. PATENT DOCUMENTS

| | | |
|---|---|---|
| 5,116,340 | 5/1992 | Songer et al. . |
| 5,123,926 | 6/1992 | Pisharodi . |
| 5,127,912 | 7/1992 | Ray et al. . |
| 5,129,388 | 7/1992 | Vignaud et al. . |
| 5,129,904 | 7/1992 | Illi . |
| 5,147,359 | 9/1992 | Cozad et al. . |
| 5,154,718 | 10/1992 | Cozad et al. . |
| 5,171,278 | 12/1992 | Pisharodi . |
| 5,176,678 | 1/1993 | Tsou . |
| 5,176,680 | 1/1993 | Vignaud et al. . |
| 5,181,917 | 1/1993 | Rogozinski . |
| 5,192,321 | 3/1993 | Strokon . |
| 5,192,327 | 3/1993 | Brantigan et al. . |
| 5,201,734 | 4/1993 | Cozad et al. . |
| 5,242,445 | 9/1993 | Ashman . |
| 5,242,448 | 9/1993 | Pettine et al. . |
| 5,246,442 | 9/1993 | Ashman et al. . |
| 5,261,909 | 11/1993 | Sutterlin et al. . |
| 5,263,953 | 11/1993 | Bagby . |
| 5,281,222 | 1/1994 | Allarad et al. . |
| 5,282,801 | 2/1994 | Sherman . |
| 5,290,312 | 3/1994 | Kojimoto et al. . |
| 5,290,494 | 3/1994 | Coombes et al. . |
| 5,303,718 | 4/1994 | Krajicek . |
| 5,304,179 | 4/1994 | Wagner . |
| 5,306,307 | 4/1994 | Senter et al. . |
| 5,306,309 | 4/1994 | Wagner et al. . |
| 5,312,405 | 5/1994 | Korotko et al. . |
| 5,312,410 | 5/1994 | Miller et al. . |
| 5,318,566 | 6/1994 | Miller . |
| 5,336,223 | 8/1994 | Rogers . |
| 5,336,240 | 8/1994 | Metzler et al. . |
| 5,344,422 | 9/1994 | Frigg . |
| 5,348,026 | 9/1994 | Davidson . |
| 5,357,983 | 10/1994 | Mathews . |
| 5,360,429 | 11/1994 | Jeanson et al. . |
| 5,360,431 | 11/1994 | Puno et al. . |
| 5,361,766 | 11/1994 | Nichols et al. . |
| 5,364,399 | 11/1994 | Lowery et al. . |
| 5,380,325 | 1/1995 | Lahille et al. . |
| 5,390,683 | 2/1995 | Pisharodi . |
| 5,395,374 | 3/1995 | Miller et al. . |
| 5,397,364 | 3/1995 | Kozak et al. . |
| 5,403,315 | 4/1995 | Ashman . |
| 5,405,391 | 4/1995 | Hednerson et al. . |
| 5,415,658 | 5/1995 | Kilpela et al. . |
| 5,417,690 | 5/1995 | Sennett et al. . |
| 5,423,820 | 6/1995 | Miller et al. . |
| 5,423,825 | 6/1995 | Levine . |
| 5,425,772 | 6/1995 | Brantigan . |
| 5,466,237 | 11/1995 | Byrd, III et al. . |
| 5,474,555 | 12/1995 | Puno et al. . |
| 5,480,437 | 1/1996 | Draenert . |
| 5,484,437 | 1/1996 | Michelson . |
| 5,489,307 | 2/1996 | Kuslich et al. . |
| 5,489,308 | 2/1996 | Kuslich et al. . |
| 5,496,318 | 3/1996 | Howland et al. . |
| 5,505,732 | 4/1996 | Michelson . |
| 5,507,746 | 4/1996 | Lin . |
| 5,514,180 | 5/1996 | Heggeness et al. . |
| 5,520,690 | 5/1996 | Errico et al. . |
| 5,522,899 | 6/1996 | Michelson . |
| 5,527,341 | 6/1996 | Gogolewski et al. . |
| 5,531,746 | 7/1996 | Errico et al. . |
| 5,531,751 | 7/1996 | Schultheiss et al. . |
| 5,536,270 | 7/1996 | Songer et al. . |
| 5,536,271 | 7/1996 | Daly et al. . |
| 5,545,165 | 8/1996 | Biedermann et al. . |
| 5,549,608 | 8/1996 | Errico et al. . |
| 5,549,612 | 8/1996 | Yapp et al. . |
| 5,554,157 | 9/1996 | Errico et al. . |
| 5,563,124 | 10/1996 | Damien et al. . |
| 5,569,248 | 10/1996 | Mathews . |
| 5,569,253 | 10/1996 | Farris et al. . |
| 5,571,192 | 11/1996 | Schönhöffer . |
| 5,575,792 | 11/1996 | Errico et al. . |
| 5,578,033 | 11/1996 | Errico et al. . |
| 5,584,834 | 12/1996 | Errico et al. . |
| 5,586,984 | 12/1996 | Errico et al. . |
| 5,593,409 | 1/1997 | Michelson . |
| 5,601,553 | 2/1997 | Trebing et al. . |
| 5,601,556 | 2/1997 | Pisharodi . |
| 5,603,713 | 2/1997 | Aust et al. . |
| 5,607,424 | 3/1997 | Tropiano . |
| 5,607,425 | 3/1997 | Rogozinski . |
| 5,607,426 | 3/1997 | Ralph et al. . |
| 5,607,430 | 3/1997 | Bailey . |
| 5,609,592 | 3/1997 | Brumfield et al. . |
| 5,609,593 | 3/1997 | Errico et al. . |
| 5,609,594 | 3/1997 | Errico et al. . |
| 5,609,596 | 3/1997 | Pepper . |
| 5,609,635 | 3/1997 | Michelson . |
| 5,609,636 | 3/1997 | Kohrs et al. . |
| 5,611,800 | 3/1997 | Davis et al. . |
| 5,611,801 | 3/1997 | Songer . |
| 5,613,967 | 3/1997 | Engelhardt et al. . |
| 5,616,144 | 4/1997 | Yapp et al. . |
| 5,620,443 | 4/1997 | Gertzbein et al. . |
| 5,624,441 | 4/1997 | Sherman et al. . |
| 5,626,579 | 5/1997 | Muschler et al. . |
| 5,628,740 | 5/1997 | Mullane . |
| 5,628,756 | 5/1997 | Barker, Jr. et al. . |
| 5,630,816 | 5/1997 | Kambin . |
| 5,632,747 | 5/1997 | Scarborough et al. . |
| 5,634,925 | 6/1997 | Urbanski . |
| 5,643,260 | 7/1997 | Doherty . |
| 5,643,264 | 7/1997 | Sherman et al. . |
| 5,643,265 | 7/1997 | Errico et al. . |
| 5,645,084 | 7/1997 | McKay . |
| 5,645,544 | 7/1997 | Tai et al. . |
| 5,645,549 | 7/1997 | Boyd et al. . |
| 5,645,598 | 7/1997 | Brosnahan, III . |
| 5,647,873 | 7/1997 | Errico et al. . |
| 5,649,927 | 7/1997 | Kilpela et al. . |
| 5,651,283 | 7/1997 | Runciman et al. . |
| 5,651,789 | 7/1997 | Cotrel . |
| 5,653,708 | 8/1997 | Howland . |
| 5,653,709 | 8/1997 | Frigg . |
| 5,653,763 | 8/1997 | Errico et al. . |
| 5,658,289 | 8/1997 | Boucher et al. . |
| 5,658,337 | 8/1997 | Kohrs et al. . |
| 5,658,516 | 8/1997 | Eppley et al. . |
| 5,662,653 | 9/1997 | Songer et al. . |
| 5,665,088 | 9/1997 | Gil et al. . |
| 5,665,112 | 9/1997 | Thal . |
| 5,665,122 | 9/1997 | Kambin . |
| 5,667,506 | 9/1997 | Sutterlin . |
| 5,667,507 | 9/1997 | Corin et al. . |
| 5,667,508 | 9/1997 | Errico et al. . |
| 5,668,288 | 9/1997 | Storey et al. . |
| 5,669,909 | 9/1997 | Zdeblick et al. . |
| 5,669,910 | 9/1997 | Korhonen et al. . |
| 5,669,911 | 9/1997 | Errico et al. . |
| 5,671,695 | 9/1997 | Schroeder . |
| 5,672,175 | 9/1997 | Martin . |
| 5,674,222 | 10/1997 | Berger et al. . |
| 5,674,295 | 10/1997 | Ray et al. . |
| 5,674,296 | 10/1997 | Bryan et al. . |
| 5,676,665 | 10/1997 | Bryan . |
| 5,676,666 | 10/1997 | Oxland et al. . |
| 5,676,701 | 10/1997 | Yuan et al. . |
| 5,676,703 | 10/1997 | Gelbard . |

| | | |
|---|---|---|
| 5,681,311 | 10/1997 | Foley et al. . |
| 5,681,312 | 10/1997 | Yuan et al. . |
| 5,683,391 | 11/1997 | Boyd . |
| 5,683,392 | 11/1997 | Richelsoph et al. . |
| 5,683,393 | 11/1997 | Ralph . |
| 5,683,394 | 11/1997 | Rinner . |
| 5,688,272 | 11/1997 | Montague et al. . |
| 5,688,273 | 11/1997 | Errico et al. . |
| 5,688,274 | 11/1997 | Errico et al. . |
| 5,688,279 | 11/1997 | McNulty et al. . |
| 5,688,280 | 11/1997 | Booth, Jr. et al. . |
| 5,690,629 | 11/1997 | Asher et al. . |
| 5,690,630 | 11/1997 | Errico et al. . |
| 5,690,631 | 11/1997 | Duncan et al. . |
| 5,690,632 | 11/1997 | Schwartz et al. . |
| 5,690,633 | 11/1997 | Taylor et al. . |
| 5,690,842 | 11/1997 | Panchison . |
| 5,693,046 | 12/1997 | Songer et al. . |
| 5,693,053 | 12/1997 | Estes . |
| 5,693,100 | 12/1997 | Pisharodi . |
| 5,697,929 | 12/1997 | Mellinger . |
| 5,697,977 | 12/1997 | Pisharodi . |
| 5,700,291 | 12/1997 | Kuslich et al. . |
| 5,700,292 | 12/1997 | Maargulies . |
| 5,702,391 | 12/1997 | Lin . |
| 5,702,392 | 12/1997 | Wu et al. . |
| 5,702,393 | 12/1997 | Pfaifer . |
| 5,702,394 | 12/1997 | Henry et al. . |
| 5,702,395 | 12/1997 | Hopf . |
| 5,702,396 | 12/1997 | Hoenig et al. . |
| 5,702,399 | 12/1997 | Kilpela et al. . |
| 5,702,449 | 12/1997 | McKay . |
| 5,702,450 | 12/1997 | Bisserie . |
| 5,702,451 | 12/1997 | Biedermann et al. . |
| 5,702,452 | 12/1997 | Argenson et al. . |
| 5,702,453 | 12/1997 | Rabbe et al. . |
| 5,702,454 | 12/1997 | Baumgartner . |
| 5,702,455 | 12/1997 | Saggar . |
| 5,704,936 | 1/1998 | Mazel . |
| 5,704,937 | 1/1998 | Martin . |
| 5,707,372 | 1/1998 | Errico . |
| 5,707,395 | 1/1998 | Hopf . |
| 5,709,681 | 1/1998 | Pennig . |
| 5,709,682 | 1/1998 | Medoff . |
| 5,709,683 | 1/1998 | Bagby . |
| 5,709,684 | 1/1998 | Errico et al. . |
| 5,709,685 | 1/1998 | Dombrowski et al. . |
| 5,709,686 | 1/1998 | Talos et al. . |
| 5,713,841 | 2/1998 | Graham . |
| 5,713,898 | 2/1998 | Stucker et al. . |
| 5,713,899 | 2/1998 | Marnay et al. . |
| 5,713,900 | 2/1998 | Benzel et al. . |
| 5,713,903 | 2/1998 | Sander et al. . |
| 5,713,904 | 2/1998 | Errico et al. . |
| 5,716,355 | 2/1998 | Jackson . |
| 5,716,356 | 2/1998 | Biedermann et al. . |
| 5,716,357 | 2/1998 | Rogozinski . |
| 5,716,358 | 2/1998 | Ochoa . |
| 5,716,359 | 2/1998 | Ojima et al. . |
| 5,716,415 | 2/1998 | Steffee . |
| 5,716,416 | 2/1998 | Lin . |
| 5,720,746 | 2/1998 | Soubeiran . |
| 5,720,747 | 2/1998 | Burke . |
| 5,720,748 | 2/1998 | Kuslich et al. . |
| 5,720,751 | 2/1998 | Jackson . |
| 5,722,977 | 3/1998 | Wilhelmy . |

OTHER PUBLICATIONS

DANEK Publication entitled, "AXIS—Fixation System," 1993, pp. 1–6.

Synthes Publication entitled, "Small Notched Titanium Reconstruction Plate System," 1996, pp. 1–6.

J. Neurosurg Publication entitled, "Posterior plates in the management of cervical instability: long–term results in 44 patients," vol. 81, 1994, pp. 341–349.

BNI Quarterly Publication entitled, "Lateral Mass Posterior Plating and Facet Fusion for Cervical Spine Instability," vol. 7, No. 2, 1991, pp. i, ii, 1–12.

Beadling, Lee, Orthopedics Today Publication entitled, "FDA Clears Spinal Cages for Interbody Lumbar Fusion," pp. 1–2, Date Unknown.

MedPro Month Publication entitled, "Trends in Spine & Disk Surgery," vol. VI, No. 11–12, pp. 280–284, Dec. 1996.

Surgical Dynamics Ray Threaded Fusion Cage Device Surgical Technique Manual, pp. 1–10, 1996.

Surgical Dynamics Ray Threaded Fusion Cage, pp. 1–6, 1996.

AcroMed Publication entitled, "AcroMed Spinal Solutions for Cervical Pathologies," 07–95, pp. 1–8.

Codman Publication entitled, "Sof'wire Cable System," 6 pp., 06–92.

Huhn, Stephen L. et al., "Posterior Spinal Osteosynthesis for Cervical Fracture/Dislocation Using a Flexible Multistrand Cable System: Technical Note," Neurosurgery, vol. 29, No. 6, pp. 943–946, 12–91.

Dickman, Curtis A. et al., "Wire Fixation for the Cervical Spine: Biomechanical Principles and Surgical Techniques," BNI Quarterly, vol. 9, No. 4, Fall 1993, pp. 2–16.

Publication by AcroMed entitled, "ACROMED Cable System by Songer," Sep. 1993, 4 pp.

M. Aebi, MD, et al., "Treatment of Cervical Spine Injuries with Anterior Plating: Indications, Techniques, and Results," vol. 16, No. 3S, Mar., 1991 Supplement, pp. S38–S45.

Foley, M.D. et al., "Aline Anterior Cervical Plating System," Smith & Nephew Richards, Inc. Orthopaedics Catalog Information, (Sep. 1996), pp. 1–16.

Lowery, Gary L., M.D., Ph.D., Sofamor Danek Group, Inc. Publication entitled, "Orion Anterior Cervical Plate System: Surgical Technique," 1994, pp. 1–24.

Apfelbaum, R., M.D., Aesculap Scientific Information publication entitled, "Posterior Transarticular C1–2 Screw Fixation for Atlantoaxial Instability," 1993, pp. 1–15.

Danek Titanium Cable System publication by Danek Group, Inc., 1994, 6 pp.

Publication entitled, "Spinal Disorders", 4 pp., Date Unknown.

O'Brien, John P., Ph.D., Orthopaedic Product News Article entitled, "Interbody Fusion of the Lumbar Spine," pp. 1–3., Date Unknown.

Roy et al., "Variation of Young's Modulus and Hardness in Human Lumbar Vertebrae Measured by Nanoindentation", pp. 1–4., date unknown.

Sofamor Danek publication entitled, "Atlas Cable System: Evolution of the Cable System for Spinal Applications," 1995, 2 pp.

AcroMed publication entitled, "AcroMed Songer Cable System: Ordering information for Implants and Instruments," (Apr. 1996), 4 pp.

Songer, Matthew, M.D., "Acromed Cable System by Songer: Cervical Technique Manual," pp. 1–17., date unknown.

Songer, Matthew N., M.D., "ACROMED Cable System by Songer: Technique Manual," 1993, pp. 1–20.

Oxland, Thomas R., Ph.D., et al., SpineTech Inc. Publication entitled, "Biomechanical Rationale—The BAK Interbody Fusion System: An Innovative Solution," pp. 1–16., 1994.

SpineTech, Inc. publication entitled, "Patient Information on Spinal Fusion Surgery and the BAK Interbody Fusion System," 10 pp., 1993.

SpineTech, Inc. publication entitled, "BAK/Cervical Interbody Fusion System," 1994, 2 pp.

SpineTech, Inc. publications entitled, "Instrumentation BAK Interbody Fusion System," "Biomechanics BAK Interbody Fusion System," and "Porosity BAK Interbody Fusion System," 1996, 12 pp.

SpineTech, Inc. publication entitled, "The BAK Interbody Fusion System," 1996, 4 pp.

Depuy Motech, Inc. publication entitled, "Moss Miami 3–Dimensional Spinal Instrumentation: Taking Spinal Instrumentation to a New Dimension," 1995, 8 pp.

Shufflebarger, Harry L., M.D., "Moss Miami Spinal Instrumentation System: Methods of Fixation of the Spondylopelvic Junction," *Lumbosacral and Spinopelvic Fixation,* 1996 by Raven Publishers, Philadelphia, pp. 381–393.

Shufflebarger, Harry L., M.D., Depuy Motech publication entitled, "Clinical Issue: Rod Rotation in Scoliosis Surgery," 5 pp., 1995.

AcroMed publication entitled, "Instruments," 3 pp., Date Unknown.

SpineTech, Inc. publication entitled, "The Bone Harvester," 1996, 2 pp.

Wright Medical Technology Publication entitled, "Versalok Low Back Fixation System," 1996, pp. 1–4.

Danek Medical, Inc. Publication entitled, "TSRH Lumbar System," 1991, pp. 1–4.

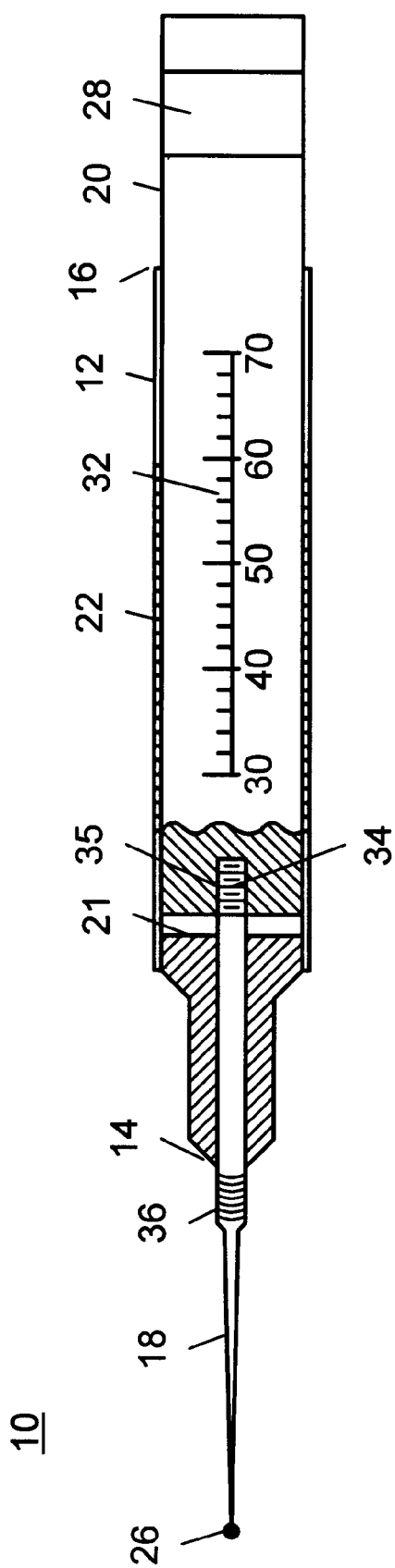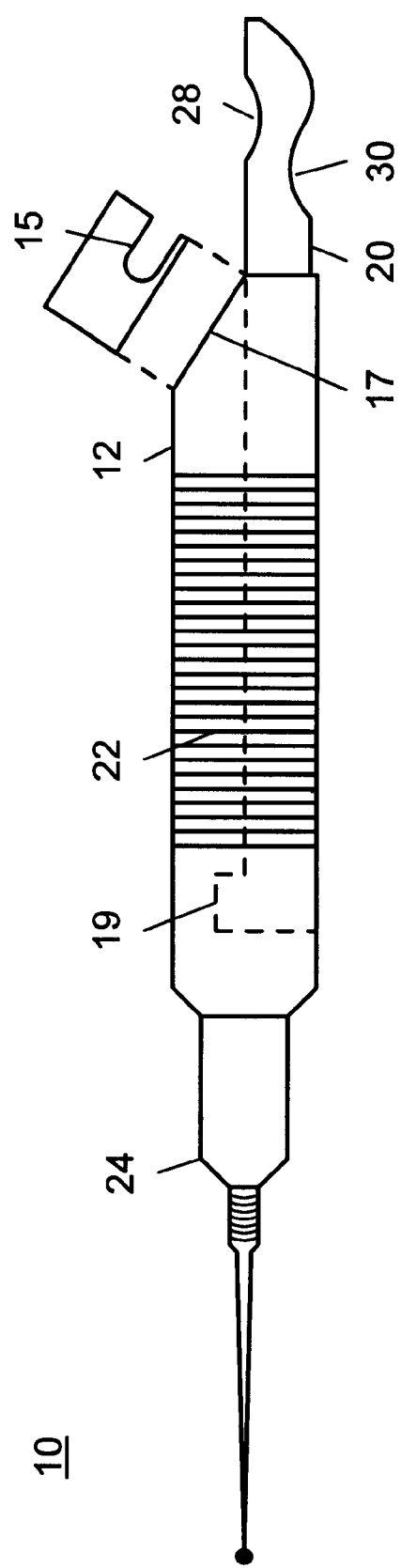

PEDICLE PROBE AND DEPTH GAGE

BACKGROUND OF THE INVENTION

1. Field of the Invention

The present invention generally relates to instruments and the like. More particularly, an embodiment of the invention relates to a bone probing device for examining holes drilled in bones to accommodate spinal implant fixation components.

2. Description of the Related Art

Spinal fixation, such as lumbar sacral fusion and the correction of spinal deformities such as scoliotic curves, is a well known and frequently used medical procedure. Pedicle, lateral, and oblique mounting devices may be used to secure corrective spinal instrumentation to a portion of the spine that has been selected to be fused by arthrodesis.

A spinal fixation system typically includes corrective spinal instrumentation that is attached to selected vertebrae of the spine by screws, hooks, and clamps. The corrective spinal instrumentation includes spinal rods or plates that are generally parallel to the patient's back. The corrective spinal instrumentation may also include transverse connecting rods that extend between neighboring spinal rods. Spinal fixation systems are used to correct problems in the lumbar and thoracic portions of the spine, and are often installed posterior to the spine on opposite sides of the spinous process and adjacent to the transverse process.

Various types of screws, hooks, and clamps have been used for attaching corrective spinal instrumentation to selected portions of the patient's spine. Examples of pedicle screws and other types of attachments are illustrated in U.S. Pat. Nos. 4,763,644; 4,805,602; 4,887,596; 4,950,269; and 5,129,388. U.S. patent application entitled "Polyaxial Spinal Fixation System and Method" having Michael C. Dinsdale and Erik J. Wagner as inventors and filed May 27, 1997 and U.S. patent application Ser. No. 08/740,123 filed Oct. 24, 1996 each relate to fixation of the human spine using pedicle screws and are incorporated by reference as if fully set forth herein.

Before a spinal implant can be attached to the spine with a pedicle screw, an opening is typically drilled into the spine to accommodate the screw. After the opening is drilled into the spine, it may be desired to determine whether drilling of the opening resulted in any cracks or openings in the interior side wall of the opening. The surgeon's field of view within such an opening tends to be limited. It is generally not possible to thoroughly examine the side wall for cracks or openings visually. Therefore, surgeons have used a pedicle probe to feel the interior side wall of the opening to locate any cracks or openings in the side wall. If it is determined that a crack or opening is present in the side wall, a new opening will typically be drilled in a different location to accommodate the screw.

After an opening has been drilled and found to be adequate upon inspection with a pedicle probe, a depth gage is typically inserted within the opening to determine its depth. Once the depth of the opening is determined, a screw having an appropriate length can be selected for insertion within the opening.

U.S. Pat. No. 5,242,448 to Pettine et al. relates to an orthopedic bone probing device to locate cavities, holes, and crevices in bones. The probing device includes "a cannula containing a shaft of superelastic material that assumes a retractable position angular to the axis of the cannula upon being ejected from one end of the cannula." See abstract. The "pre-conditioned 'J' shaped shaft" may return to the "J" shape when it is extended beyond the tip of the cannula. Surgeons have experienced difficulty inserting conventional rigid rods having a curve or hook at the end into bone holes having a relatively small diameter. Pettine et al.'488 states "the value of the retractable probe is its ability to be inserted into small openings in the bone and then be extended out to serve as a useful bone probe." See Background and Summary of the Invention.

SUMMARY OF THE INVENTION

In accordance with the present invention, a bone probing device is provided that is capable of measuring the depth of an opening in a bone during the same surgical step that the surgeon probes the interior of the opening.

An embodiment of the invention relates to a bone probe that includes a body, a shaft for contacting an interior portion of a bone opening, and an arm for adjusting the shaft. The shaft and arm are preferably slideably mounted within the body and extend from opposite sides of the body. The arm and shaft are preferably connected such that the arm is capable of being adjusted to retract or extend the shaft from an end of the body. The body preferably includes one or more stopping portions within its interior to define the range of motion of the arm and/or shaft through the body. The arm may include a stopper that inhibits it from being completely removed from the body.

The shaft preferably includes a probing end for contacting an interior portion of a bone. The probing end may include a substantially curvate head to minimize any tissue irritation that occurs during probing of the bone opening. The shaft is preferably substantially flexible to allow the surgeon to apply pressure against the interior sidewall of the bone opening without damaging the bone. The shaft, however, is also preferably sufficiently rigid and substantially non-elastic to provide a proper "feel" to the surgeon to allow him/her to locate any irregularities on the surface of the interior sidewall. The shaft may be tapered such that it narrows in a direction toward the probing end whereby the flexibility of the shaft increases toward the probing end.

The arm preferably includes a plurality of reference markings on its surface for measuring a depth of the bone opening. The reference markings may be read to provide the distance between the probing end and a first end of the body, which approximates the depth of the bone opening. The arm may contain indentions on its top and bottom surfaces that are sized to receive a human finger or thumb to facilitate adjustment of the arm.

The arm and the shaft are preferably removably coupled. The arm preferably includes a first threaded surface and the shaft preferably includes a second threaded surface that is complementary to that of the arm to allow the arm and shaft to be screwed together. After a predetermined number of uses, the shaft may be unscrewed from the arm and a new shaft may be screwed onto the arm. The shaft may include a roughened portion and/or a portion having an enlarged diameter to facilitate connection of the shaft and the arm.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIG. 1 depicts a top view partially in section of an embodiment of a bone probe in accordance with the present invention.

FIG. 2 depicts a side view of the bone probe of FIG. 1.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

A top view of an embodiment of a bone probe 10 is depicted partially in section in FIG. 1. The bone probe preferably includes a body 12 having a first end 14 and a second end 16. The body is preferably substantially cylindrical and hollow. The body preferably includes an interior chamber for containing shaft 18 and arm 20. The body may contain a plurality of protrusions or indentions 22 on its surface to provide a friction surface to be gripped by the surgeon when the bone probe is inserted within the surgical wound. Each of the body, shaft, and arm are preferably constructed of stainless steel, but such components may instead be made of other materials such as plastic, titanium, and suitable metal alloys.

Shaft 18 is preferably slideably mounted within the body such that it is extendable from and insertable into first end 14. The shaft may extend from a substantially cylindrical head 24 of the body located proximate first end 14. The head 24 may have a reduced diameter as compared to the remainder of the body. The shaft preferably includes a probing end 26 for contacting an interior surface of an opening in a bone. The probing end preferably includes a substantially curvate head that aids the surgeon in detecting surface irregularities on the interior surface of the bone opening. Such surface "irregularities" may include cracks, crevices, cavities, or other openings. A surgeon may probe the interior wall of a bone opening to determine whether the wall has been cracked during drilling of the bone opening. The curvate head may also aid the surgeon in probing threads drilled onto the interior surface of the opening in the bone. The curvate head preferably lessens or eliminates any tissue irritation that otherwise tends to occur when a sharper object is used to probe the bone opening.

At least a portion of the shaft is preferably substantially flexible or semi-rigid to provide a proper "feel" to the surgeon during examination of the bone opening. The shaft is preferably substantially non-elastic such that the surgeon can apply pressure against the interior wall of a bone opening to feel for irregularities. The shaft is preferably tapered such that it narrows in a direction toward the probing end. In this manner, the flexibility of the shaft may increase along the shaft in a direction toward the probing end.

Arm 20 is preferably connected to the shaft and capable of sliding within body 12. The arm is preferably extendable from and insertable into second end 16. The arm is preferably moveable to cause the shaft to move relative to the first end 14 during use. The arm preferably includes an indention 28 on its upper surface and an indention 30 on its lower surface. Each of the indentions 28 and 30 are preferably sized to receive a human finger or thumb to facilitate grasping of the arm by the surgeon. The arm preferably includes a plurality of reference markings 32 for allowing the surgeon to determine the depth of the bone opening. A plurality of numerals may be located adjacent to the reference markings as shown in FIG. 1. The reference markings are preferably alignable with the second end 16 to allow the distance from the probing end to first end 14 to be determined. Head 24 is preferably placed at the entrance of the bone opening and the probing end is preferably extended to the terminus of the bone opening such that the distance from the probing end to first end 14 approximates the depth of the bone opening. The body preferably comprises a notch 15 in its surface proximate second end 16 such that the reference markings are observable through the notch. It is to be understood that the spacing between reference markings and particular numerals may be different that those depicted in FIG. 1.

In an embodiment of the invention, the shaft includes first threaded surface 34 and the arm includes second threaded surface 35 for forming a complementary engagement with the threaded surface of the shaft. The threading on each of the shaft and the arm may be external male threading or internal female threading. In this manner, the shaft and the arm may be removably coupled to one another. Conventional bone probes are typically discarded periodically after a selected number of uses. The removable engagement between the shaft and the arm allows the shaft to be removed and replaced with a new shaft. Thus only the shaft need be periodically replaced. It is to be understood that the shaft and arm may be removably engaged in various other ways as well. For instance, a reversible snap-fit engagement may be formed between the shaft and arm.

The shaft may include a coupling portion 36 between the threading 34 and the tapered portion of the shaft. The coupling portion may have a greater diameter than the tapered portion and is preferably substantially non-flexible. The coupling portion may include a roughened or friction surface that serves as a grasping region to enable the surgeon to more easily rotate the shaft during connection of the shaft and arm. The roughened surface may include a plurality of grooves or protrusions.

The movement of the arm and shaft are preferably limited within the body to prevent the arm or shaft from being completely removed from the body. The body preferably comprises a chamfered edge 17 proximate the second end. In one embodiment, the arm includes one or more stoppers 19 extending therefrom to contact a portion of the body proximate the first end 14 and/or second end 16 to inhibit the arm from being (a) completely removed from the second end and/or (b) inserted through the first end. The chamfered edge may contact stopper 19 when the arm is fully extended from second end 16. The body may include one or more stopping portions (e.g., stopping portion 21) extending from its interior surface that contact the stopper(s) on the arm to define the range of motion of the arm and shaft within the body The arm preferably contacts the interior portion of the body such that friction between the arm and the body provides a substantial resistance to axial motion of the arm within the body. To create friction between the body and the arm, the body may contain (a) grooves into which the arm may fit or (b) a guide along the interior surface of the body that is adapted to fit on one or both sides of the arm. The grooves or guide may inhibit movement of the arm in a direction perpendicular to the longitudinal axis of the body. In the absence of a force of predetermined magnitude applied to the arm or shaft, the friction preferably maintains the arm and the shaft at selected location relative to the body.

Upon application of sufficient force to the arm, the friction is preferably overcome such that the shaft and arm move relative to the body. In this manner, the shaft can be extended from the body at a selected length and the surgeon can probe the interior surface of the bone opening without the shaft moving axially with respect to the body.

In operation, the head 24 of the body is preferably placed in contact with the entrance of a bone opening that has been drilled at a predetermined location on the bone. The shaft of the bone probe is preferably inserted within the opening, and the arm is preferably adjusted to move the shaft until the probing end contacts the terminus of the opening. The depth of the opening can then be determined by taking a reading from the reference marking that is aligned with the edge of second end 16. Once the surgeon has determined the depth of the hole, a screw of appropriate length may be selected for insertion into the bone opening. Without removing the bone probe from the opening, the surgeon may explore the interior wall of the bone opening with the probing end of the shaft to locate any surface irregularities. In this manner, the surgical steps of (a) measuring the depth of the bone opening and (b) probing the interior wall of the bone opening may be performed with a single instrument in one surgical step. During the probing of the wall, the surgeon may elect to slide the arm within the body to alter the length of the shaft portion that extends from the first end of the body. In the absence of significant surface irregularities, a screw may be inserted within the bone opening.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A bone probe, comprising:
    a body comprising a first end and a second end;
    a shaft slideably mountable within the body and adapted to extend from the first end during use, the shaft comprising a probing end for contacting an interior portion of a bone during use, at least a portion of the shaft proximate the probing end being substantially flexible; and
    an arm for moving the shaft during use, the arm being connected to the shaft during use and being adapted to extend from the second end during use, the arm being slideable within the body to extend and retract the shaft from the first end during use, the arm comprising a plurality of reference markings for determining a depth within the bone during use;
    wherein the shaft is configured to be removably coupled to the arm during use.

2. The bone probe of claim 1 wherein the shaft comprises a first threaded end, and wherein the arm comprises a second threaded end, the first threaded end and second threaded end being complementary to one another.

3. The bone probe of claim 1 wherein the shaft comprises a threaded end opposite the probing end, and wherein the probing end contains a curvate head for contacting the interior portion of the bone during use.

4. The bone probe of claim 1 wherein the shaft is capable of being rotated to form a fixable engagement between the shaft and the arm during use, and wherein the shaft further comprises a roughened surface to facilitate manual rotation of the shaft during use.

5. The bone probe of claim 1 wherein at least a portion of the shaft is tapered such that the tapered portion narrows in a direction toward the probing end.

6. The bone probe of claim 1 wherein the shaft is substantially non-elastic.

7. The bone probe of claim 1 wherein the arm comprises an indention sized to receive a human finger to facilitate adjustment of the arm during use.

8. The bone probe of claim 1 wherein the arm comprises a top surface and a bottom surface, each of the top surface and the bottom surface comprising an indention sized to receive a human finger to facilitate adjustment of the arm during use.

9. The bone probe of claim 1 wherein the body comprises a surface having a plurality of indentions to facilitate gripping of the body during use.

10. The bone probe of claim 1, further comprising a stopper disposed within the body, the stopper being adapted to contact the arm to inhibit the arm from being removed from the body during use.

11. The bone probe of claim 1 wherein the first end comprises a substantially cylindrically shaped receiving head for receiving the shaft, the receiving head having a diameter smaller than that of at least a portion of the body.

12. The bone probe of claim 1 further comprising a notch disposed in the body proximate the second end, and wherein at least one of the reference markings is observable through the notch during use.

13. A bone probe, comprising:
    a body comprising a first end, a second end, and a hollow portion;
    a shaft slideably mounted within the hollow portion and extending from the first end, the shaft comprising a probing end for contacting an interior portion of a bone, the shaft being tapered such that it narrows in a direction toward the probing end; and
    an arm for moving the shaft, the arm being connected to the shaft and extending from the second end, the arm being slideable within the body to extend and retract the shaft from the first end, the arm comprising a plurality of reference markings for determining a depth within the bone;
    wherein the shaft is configured to be removably coupled to the arm during use.

14. The bone probe of claim 13 wherein the shaft comprises a first threaded end, and wherein the arm comprises a second threaded end, the first threaded end and second threaded end being complementary to one another.

15. The bone probe of claim 14 wherein the probing end comprises a curvate head for contacting the interior portion of the bone during use.

16. The bone probe of claim 13 wherein the shaft is capable of being rotated to form a fixable engagement between the shaft and the arm during use, and wherein the shaft further comprises a roughened surface to facilitate manual rotation of the shaft during use.

17. The bone probe of claim 13 wherein the arm comprises an indention sized to receive a human finger to facilitate adjustment of the arm during use.

18. The bone probe of claim 13 wherein the arm comprises a top surface and a bottom surface, each of the top surface and the bottom surface comprising an indention sized to receive a human finger to facilitate adjustment of the arm during use.

19. The bone probe of claim 13 wherein the body comprises a surface having a plurality of indentions to facilitate gripping of the body during use.

20. The bone probe of claim 13, further comprising a stopper disposed within the body, the stopper being adapted to contact the arm to inhibit the arm from being removed from the body during use.

21. The bone probe of claim 13 wherein the first end comprises a substantially cylindrically shaped receiving head for receiving the shaft, the receiving head having a diameter smaller than that of at least a portion of the body.

22. The bone probe of claim 13 further comprising a notch disposed in the body proximate the second end, and wherein at least one of the reference markings is observable through the notch during use.

* * * * *